United States Patent
Robinson

[11] Patent Number: 6,149,630
[45] Date of Patent: Nov. 21, 2000

[54] SYRINGE WITH SQUEEZE RELEASE NEEDLE GUARD

[75] Inventor: Philip J. Robinson, Sylvania, Ohio

[73] Assignee: Owens-Illinois Closure Inc., Toledo, Ohio

[21] Appl. No.: 09/336,936

[22] Filed: Jun. 21, 1999

[51] Int. Cl.[7] .............................. A61M 5/32; A61M 5/00
[52] U.S. Cl. .......................................... 604/198; 604/110
[58] Field of Search ................................... 604/192, 263, 604/110, 162, 198, 187; 128/919

[56] References Cited

U.S. PATENT DOCUMENTS

| | | | |
|---|---|---|---|
| 4,631,057 | 12/1986 | Mitchell | 604/198 |
| 4,897,083 | 1/1990 | Martell . | |
| 4,947,863 | 8/1990 | Haber et al. | 604/110 |
| 5,226,894 | 7/1993 | Haber et al. | 604/198 |
| 5,338,303 | 8/1994 | King et al. . | |
| 5,338,310 | 8/1994 | Lewandowski . | |
| 5,674,203 | 10/1997 | Lewandowski | 604/197 |
| 5,713,871 | 2/1998 | Stock | 604/192 |
| 5,735,823 | 4/1998 | Berger | 604/192 |
| 5,855,839 | 1/1999 | Brunel | 264/524 |

Primary Examiner—Sharon Kennedy

[57] ABSTRACT

A syringe (10) for drawing blood from a patient, the syringe having a barrel (12) with a restricted free end (12a) and a needle assembly (14) releasably secured to the restricted free end. A plunger (16) is inserted into the barrel through an opposed end (12b), and retraction of the plunger within the barrel, away from the restricted free end, is effective to withdraw blood from the patient when a needle (14a) with a sharpened free end of the needle assembly is appropriately inserted into the patient. The syringe 10 is also provided with an annular needle guard (18) that surrounds the barrel and is slidable with respect thereto between a first position, in which the needle guard does not surround the needle, and a second position, in which the needle guard does surround the needle, to prevent the tip of the needle from injuring a person handling the syringe during times when the syringe is not being used to withdraw blood from a patient. The needle guard is made from a semi-rigid, transparent organic material, and has a diametrically opposed pair of inwardly extending projections (18a) that engage a diametrically opposed pair of outwardly facing recesses (14a) in the needle assembly when the needle guard is in its first position to prevent it from inadvertently moving to its second position. Hand squeezing of the needle guard along an axis extending perpendicularly to an axis between the projections is effective to disengage the projections and recesses, whereupon relative motion can occur between the barrel and the needle guard.

9 Claims, 4 Drawing Sheets

SYRINGE WITH SQUEEZE RELEASE NEEDLE GUARD

BACKGROUND OF THE INVENTION

1. Field of the Invention

This invention relates to a syringe of the type used to draw blood from a patient. More particularly, this invention relates to a syringe of the foregoing character which has a telescoping needle guard that is released by squeezing, after the drawing of blood from the patient, to protect medical personnel from injurious contact with a sharp tip of the needle that is a part of such a syringe.

2. Description of the Prior Art

Various types of syringes with telescoping needle guards are described in various issued patents, for example, in U.S. Pat. No. 4,897,083 (Martell), U.S. Pat. No. 5,338,303 (King et al.) and U.S. Pat. No. 5,338,310 (Lewandowski). A characteristic of these and other types of blood drawing syringes with telescopic needle guards is that the person using any such syringe must use two hands to telescope the guard relative to the syringe, after using the syringe to draw blood from a patient.

SUMMARY OF THE INVENTION

A blood drawing syringe according to the present invention has an annular needle guard that surrounds and is telescopic with respect to the exterior of the body of the syringe, the needle guard being retracted from surrounding contact with a needle of the syringe during the use of the syringe to draw blood from a patient. The guard is manufactured from a transparent organic material to permit capacity graduations on the needle to be read by the user, and it has sufficient flexibility to be distortable in its configuration under the pressure of a single hand of the user. In its unsqueezed condition the sleeve has a series of spaced apart inwardly projection lugs that are received in a corresponding series of inwardly extending recesses of a needle containment fitment at the end of the syringe barrel to positively retain the sleeve in a position where it does not interfere with the use of the syringe. However, squeezing of the sleeve will distort its shape to the point that its lugs do not engage the fitment, and then the needle can readily move to a position relative to the sleeve where the needle will be guarded, and will do so by gravity if the syringe is held vertically with the needle up. Thus, the requisite relative motion between the needle and the sleeve, from the original locked position of the sleeve, where the sleeve does not guard the needle, to the guarding position of the sleeve can be accomplished by a step that only requires action by a single hand of the user.

Accordingly, it is an object of the present invention to provide an improved blood drawing syringe. More particularly, it is an object of the present invention to provide a blood drawing syringe of the foregoing character in which the needle of such syringe can be readily guarded, after the drawing of blood, to prevent accidental contact of an exposed needle by personnel involved in its handling. Even more particularly, it is an object of the present invention to provide a blood drawing syringe of the foregoing character in which the guarding of the needle is accomplished by a sleeve that is provided with a syringe and is moveable relative to a barrel of the syringe from a position where the sleeve does not guard the needle to a position where the sleeve does guard the needle.

For a further understanding of the present invention and the objects thereof, attention is directed to the drawing and the following brief description thereof, to the detailed description of the preferred embodiment of the invention, and to the appended claims.

DETAILED DESCRIPTION OF THE PREFERRED EMBODIMENT

Figure 1:
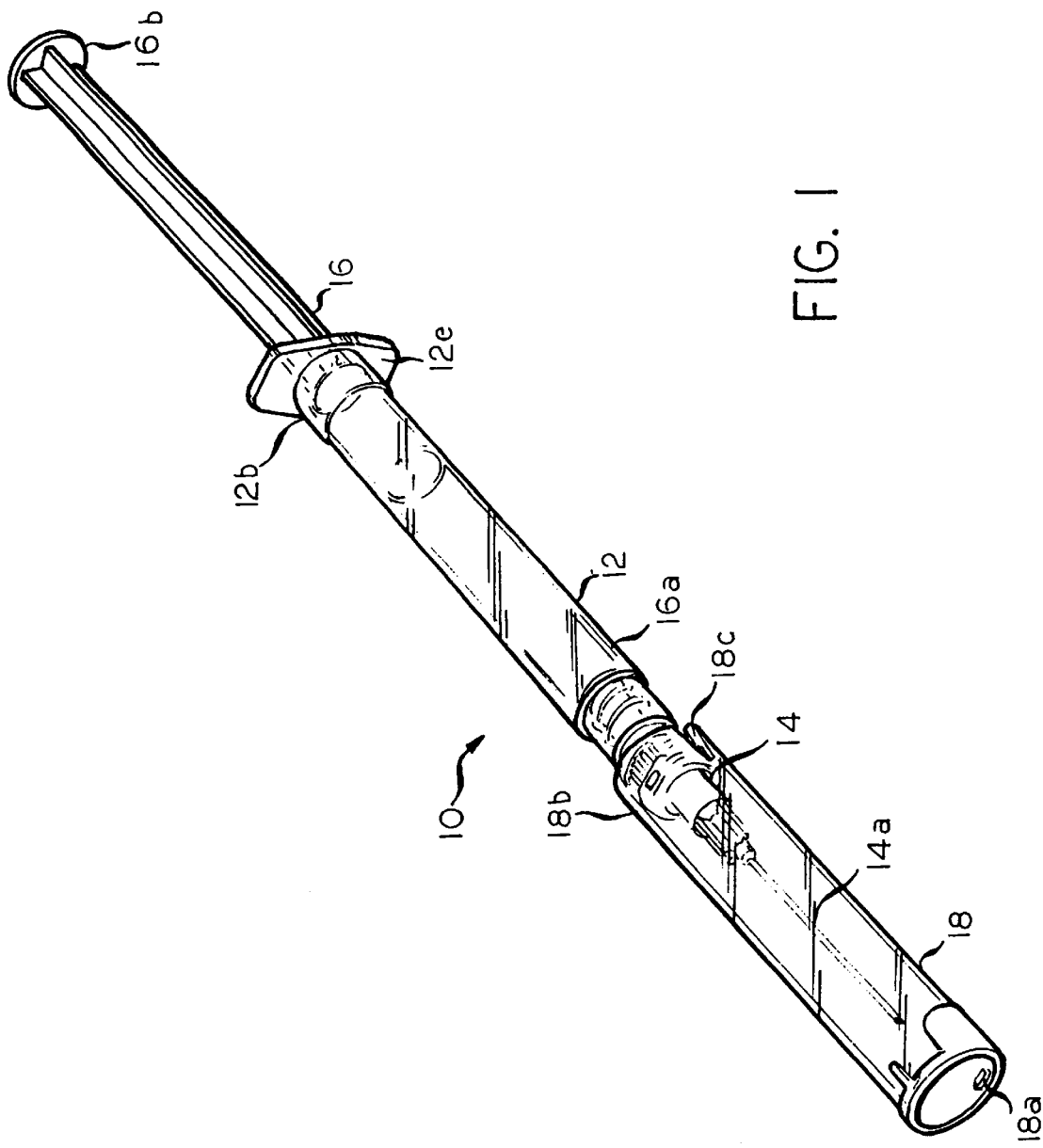
FIG. 1 is a perspective view of a syringe according to the preferred embodiment of the present invention in its position, after usage.

A syringe according to the preferred embodiment of the present invention is identified generally by reference numeral 10, and the syringe 10 includes an annular molded plastic barrel 12 with a needle assembly 14 removably secured to a restricted free end 12a of the barrel and a plunger 16 that is slidably inserted in an opposed end 12b of the barrel 12, the opposed end 12b having an opposed set of outwardly projecting tabs 12e to facilitate handling of the syringe 10. The plunger 16 has a cylindrical portion 16a at a free end that is within the barrel 12, and serves to draw blood from a patient through the needle assembly 14 when the plunger 16 is drawn away from the needle assembly 14. In that regard, the plunger 16 has an enlarged gripping portion 16b at an opposed end. While the plunger 16 is slidable with respect to the barrel 12, there is very little clearance between the outside diameter of the cylindrical portion 16a and the inside diameter of the barrel 12, to thereby ensure that the retraction of the plunger 16 will be effective to create the negative pressure that is needed to withdraw blood from a patient. The barrel 12 is also provided with an annular extension 12c that surrounds a portion of the restricted free end 12a and defines an annular space with the restricted free end 12a. The annular extension 12c has a helical thread 12d on its inside wall by which the needle assembly 14 is thereby releasably secured to the barrel 12. The annular extension 12c with the helical thread 12d is of the type that is referred to as a "standard locking luer" and conforms to an ANSI/HIMA MD 70.1—1983 specification.

Figure 2:
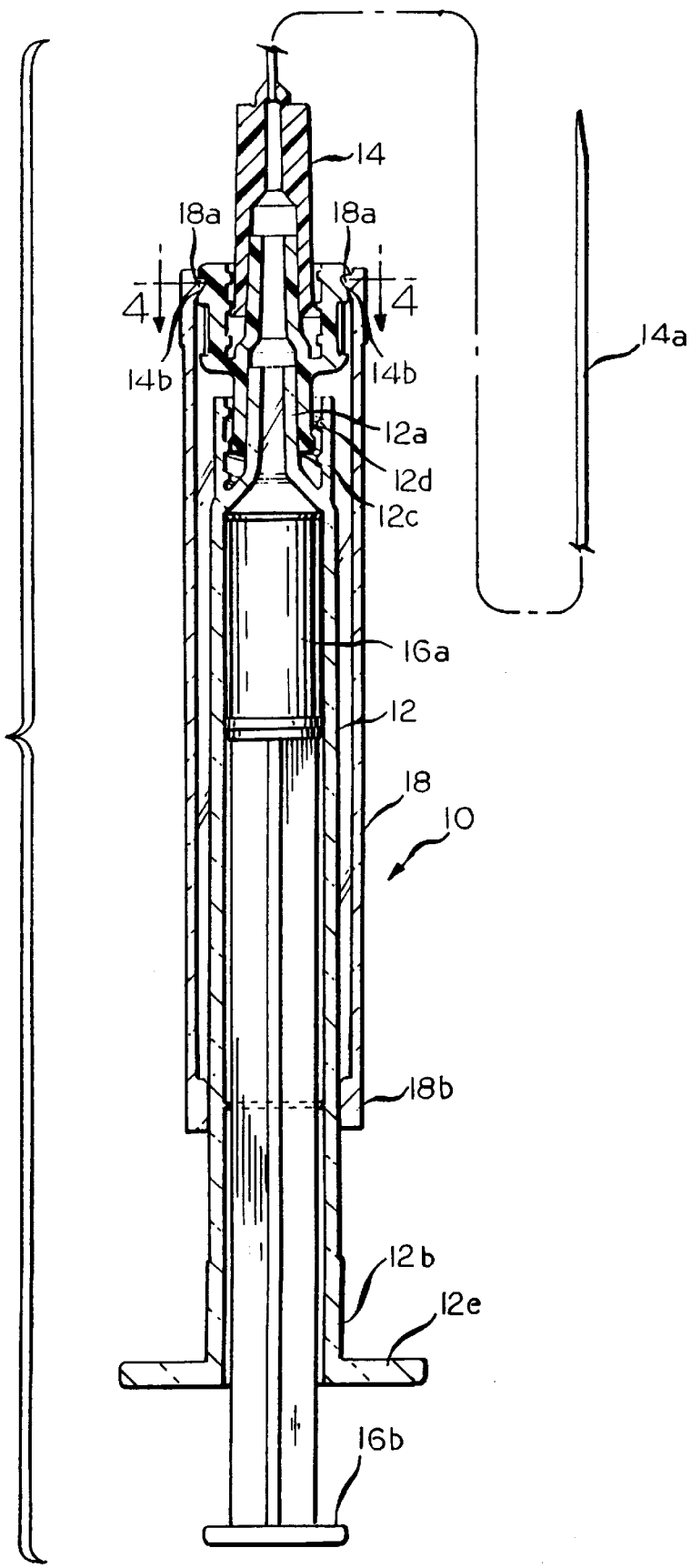
FIG. 2 is an elevational view, in cross-section and at an enlarged scale, of the syringe of FIG. 1 in a position of such syringe when it is ready for use.
Figure 3:
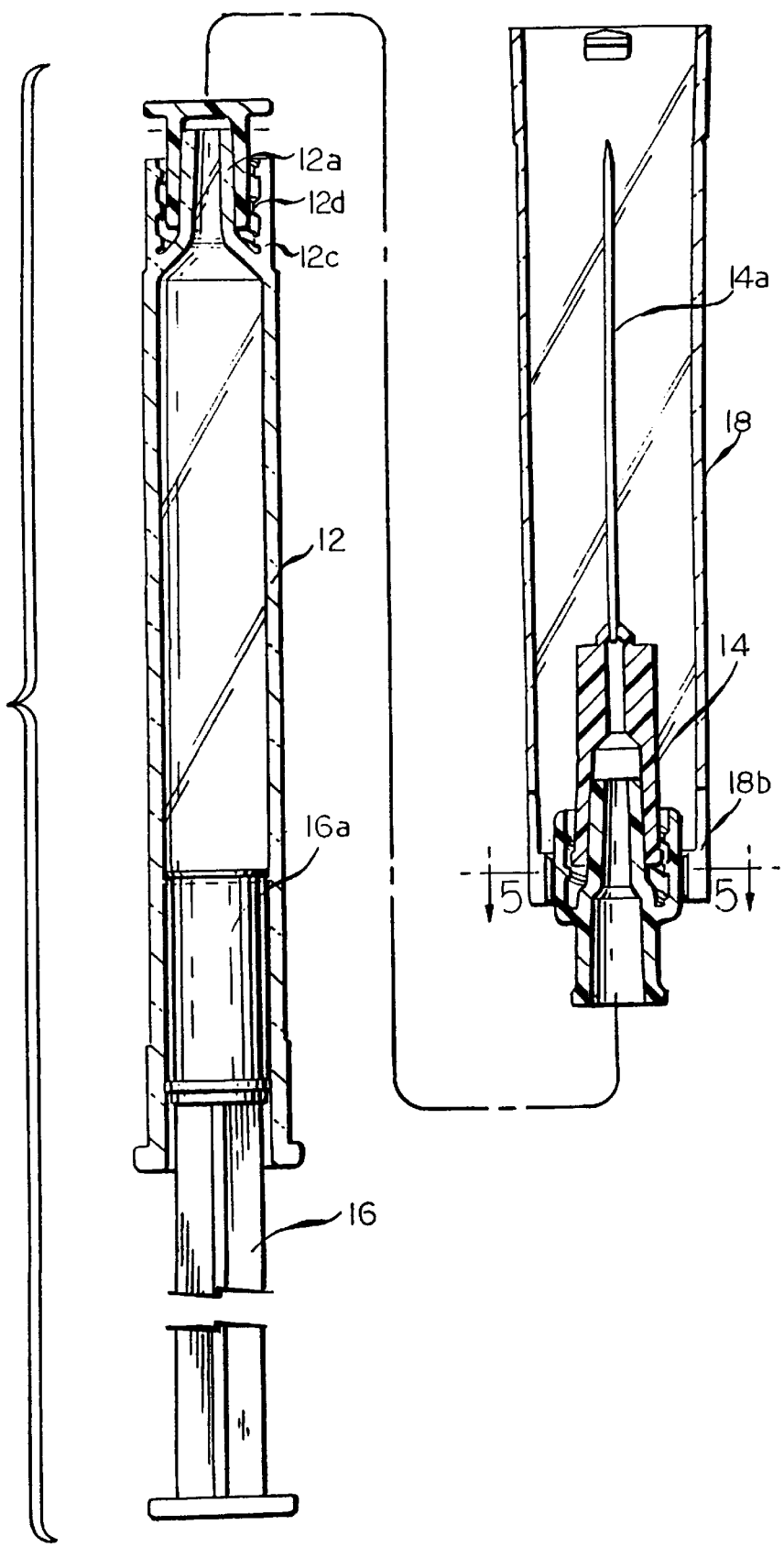
FIG. 3 is a view like FIG. 2 of the syringe of FIGS. 1 and 2 after completion of its use.
Figure 5:
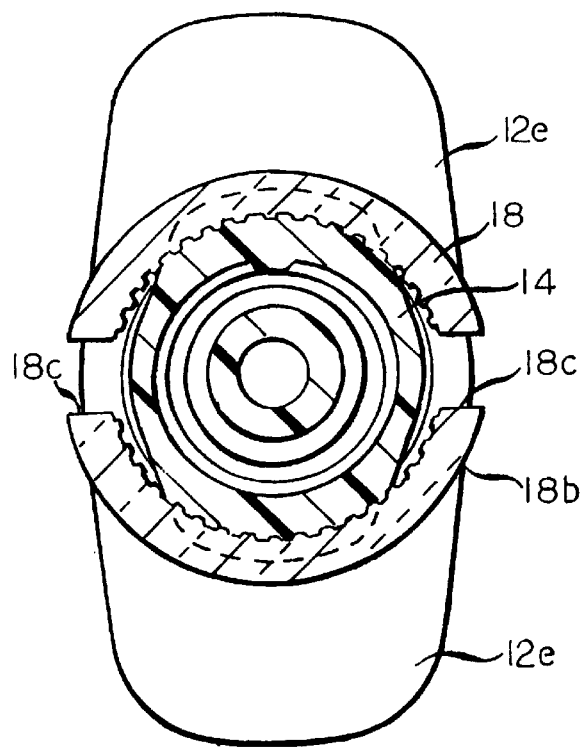
FIG. 5 is a sectional view taken on line 5—5 of FIG. 3.

The syringe 10 is also provided with an annular needle guard 18 that surrounds the barrel 12 of the syringe 10 and is slidable with respect to the barrel 12 between a first position, as shown in FIGS. 1 and 3, where the needle guard surrounds a needle element 14a of the needle assembly 14 to prevent contact between a sharpened free end of the needle 14a and any person involved in handling the syringe 10, and a second position, as shown in FIG. 2, which is its initial position, where the needle guard 18 is well away from surrounding contact with respect to the needle 14a of the needle assembly 14 to permit the user to properly use the syringe 10 to draw blood from a patient. In that regard, the needle guard 18 is preferably molded from a suitable transparent organic material to permit a user to inspect any volumetric markings on the barrel 12 (not shown) and to determine if any blood splashing is occurring during the drawing of blood. The needle guard 18 is also of a semi-rigid material to permit it to be temporarily distorted from its original circular configuration, under hand pressure, for reasons that will be hereinafter explained more fully. A gamma ray sterilized, clarified polypropylene is a suitable resin for the manufacture of the needle guard to permit it to properly perform all required functions, and it is preferred that such needle guards be packaged in blister packs and then sterilized before shipment to users. In any case, it is preferred that the needle guard 18 and the barrel 12 be formed of dissimilar organic materials to avoid binding than can occur when like organic elements must be moved relative to one another.

Figure 4:
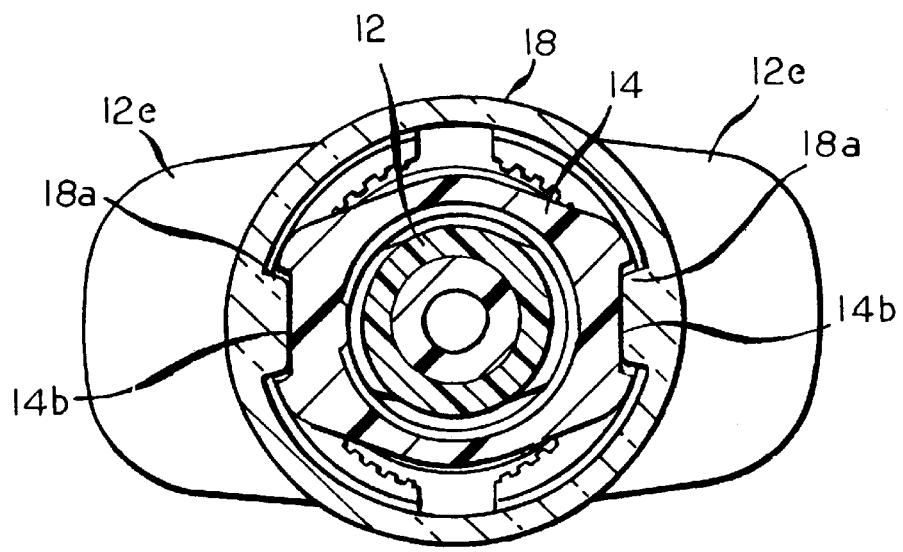
FIG. 4 is a sectional view taken on line 4—4 of FIG. 2.

The needle assembly 14 is provided with a diametrically opposed pair of inwardly extending recesses 14b that receive a diametrically opposed pair of inwardly extending projections 18a of the needle guard 18, when the needle guard 18 is at its innermost, non-guarding position, as shown in FIGS. 2 and 4, to prevent inadvertent movement of the needle guard 18 to its guarding position of FIG. 3. However, by the application of hand pressure to the needle guard 18 at opposed locations, along an axis that extends perpendicularly to the axis that extends between the projections 18a, the projections 18a will disengage from the recesses 14a to allow the needle guard 18 to move to its guarding position. This can happen at the conclusion of the blood drawing process if the user grasps the syringe 10 at a location along the axis that extends perpendicularly to the axis between the projections 18a, which can be done in a one-hand motion, and if this is done while the syringe 10 is held in a substantially vertical position with the needle 14a pointing up, this will happen by gravity as the barrel 12 then retracts relative to the needle guard 18. At that time, an added manipulative step, which can be performed by hand, may be required to ensure that the needle guard 18 has frictionally locked into its FIG. 3 guarding position. In the guarding position of the needle guard 18 relative to the barrel 12, the needle guard 18 is frictionally held in position relative to the barrel 12 by an interference fit between a thickened free end 18b of the needle guard 18 that is opposed to the end with the projections 18a and an exterior surface of the needle assembly 14, the end 18b being provided with an opposed pair of slots 18c that extend partly from the free end 18b toward the projections 18a to permit the free end 18b to expand to the extent necessary to securely grip the needle assembly 14. Further, the inside surface of the end 18b of the needle guard 18 is preferably splined and the exterior surface of the needle assembly 14, at the location of its engagement with the end 18b of the needle guard 18 in the guarding position of the needle guard 18, is complementally splined to prevent relative rotation between the needle guard 18 and the barrel 12 in the guarding position of the needle guard 18, other than to unscrew the needle assembly 14 from the barrel 12 when desired.

It is also contemplated that the syringe 10 can be provided with a separate, removable sheath (not shown) to cover the needle 14a in its FIG. 2 condition until the syringe 10 is ready for use and with an elastomeric plug (also not shown) to be inserted into the restricted free end 12a of the barrel, after the use of the syringe 10 to draw blood, and the needle assembly 14 is ready to be unscrewed from the barrel 12, as described above until the filled syringe 10 is ready to be emptied.

Although the best mode contemplated by the inventor for carrying out the invention as of the filing date hereof has been shown and described herein, it will be apparent to those skilled in the art that suitable modifications, variations and equivalents may be made without departing from the scope of the invention, such scope being limited solely by the terms of the following claims and the legal equivalents thereof.

What is claimed is:

1. A blood drawing syringe comprising:
   an originally empty barrel;
   needle means connected to an end of said barrel for drawing blood from a patient into said barrel;
   a plunger positioned within said barrel, said plunger being slidable within said barrel away from said needle means;
   a needle guard formed of a squeezable semi-rigid organic material surrounding said barrel, said needle guard being slidable with respect to said barrel from a first position, in which said needle guard does not surround said needle means, to a second position, in which said needle guard does surround said needle means; and
   locking means normally retaining said needle guard in said first position with respect to said barrel, said locking means comprising radially projecting means on one of said needle guard and said needle means and radially facing recess means on the other of said needle guard and said needle means, said radially projecting means normally engaging said radially facing recess means to prevent said needle guard from moving with respect to said barrel, said spaced apart radially projecting means and said radially facing recess means being disengagable, after drawing blood from a patient, by squeezing said needle guard to disengage said radially projecting means and said radially facing recess means to permit said needle guard to move with respect to said barrel from said first position to said second position, such disengagement being capable of accomplishment by gravity when the syringe is held in a substantially vertical position with the needle means pointing up by a step that only requires action by a single hand of a user.

2. A syringe according to claim 1 wherein said radially facing recess means comprises a diametrically opposed pair of recesses and said radially projecting means comprises a diametrically opposed pair of projections.

3. A syringe according to claim 2 wherein said needle means comprises said diametrically opposed pair of recesses and said needle guard comprises said diametrically opposed pair of projections.

4. A syringe according to claim 1 wherein said semi-rigid organic material is transparent.

5. A syringe according to claim 3 wherein said needle guard has a first end and a second end, wherein said diametrically opposed pair of projections of said needle guard is adjacent said one of said first end and said second end, and where in the other of said first end and said second end of said needle guard has means for frictionally engaging said needle means in said second position of said needle guard.

6. A syringe according to claim 5 wherein said means for frictionally engaging comprises, at said other of said first end and said second end of said needle guard, a radially thickened portion and a diametrically opposed pair of slots extending from a free end of said other of said first end and said second end of said needle guard partly to said one of said first end and said second end of said needle guard.

7. A needle guard according to claim 6 wherein said radially thickened portion has means on an interior surface for engaging means on an exterior surface of said needle means for preventing rotation of said needle guard with respect to said needle means in said second position of said needle guard.

8. A syringe according to claim 7 wherein said means on an interior surface comprises a splined surface and said means on an exterior surface comprises a complementally splined surface.

9. A syringe according to claim 1 wherein said semi-rigid organic material is mainly comprised of clarified polypropylene and wherein said needle guard is transparent.

* * * * *